United States Patent [19]

Saville

[11] Plant 4,598

[45] Sep. 30, 1980

[54] ROSE PLANT

[76] Inventor: F. Harmon Saville, 58 Hammond St., Rowley, Mass. 01969

[21] Appl. No.: 49,421

[22] Filed: Jun. 18, 1979

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose of hybrid-tea shaped blooms of unusual coloring.

1 Drawing Figure

The present invention relates to a new and distinct variety of rose plant of the miniature rose class, which was originated by my crossing as seed parent the rose known as "Rise 'N Shine" and the rose known as "Sheri Anne" as pollen parent.

Among the novel characteristics possessed by this new variety which distinguish it from its parents and all other varieties of which I am aware are its unique coloring and classic hybrid tea form with most blooms produced one to a stem in a manner typical of hybrid tea plants. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of unique salmon or carrot red coloring with singly-borne blooms of high centered, hybrid-tea like form. The flowers are unusually well formed, for a miniature rose and the singly borne flowers are well suited for cutting.

The accompanying drawing shows typical specimens of the vegetative growth and flowers of the new variety in different stages of development and is depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "27A" is plate 27A of the Royal Horticultural Society Color Chart.

Parentage: Seedling.

*Seed parent.*—"Rise 'N Shine".

*Pollen parent.*—"Sheri Anne".

Class: Miniature.

The following observations are made of specimens grown in a green house in Essex County, Mass., during the month of April.

FLOWER

Blooming habit: Fast, recurrent.

A. Bud:

(1) *Size.*—Medium.

(2) *Form.*—Ovate-pointed.

(3) *Color.*—When sepals first divide — generally 158B because underside of petals are seen first and they tend to be light colored off-white but can be infused with pink or yellow orange (salmon) tones and, sometimes, pink.

(4) *Sepals.*—Relatively short, smooth.

(5) *Peduncle.*—Length — about ¾ to 1-inches, good proportion to bloom. Aspect — straight. Strength — erect, strong. Color — 144C.

B. Bloom:

(1) *Size.*—Average size when fully expanded — about 1–1¼ to 1–1½ inches.

(2) *Borne.*—Primarily singly, occasionally smaller sprays.

(3) *Form.*—High centered at first, becoming flat upon opening, petals quill slightly at maturity.

(4) *Petalage.*—Number of petals under normal conditions — about 15 to 18.

(5) *Color.*—(During first two days). Color is difficult to describe and varies depending on lighting; when orange tones predominate, color can be 27-A to B and 29-C to D; when pink tones predominate, color can be 37-B to D and 38-B to D. The open bloom is generally 20C to 19D and older blooms, on aging, whiten to 155D with some light pink 36D tips and occasionally a color which seems to be a combination of 155D and 36D. The color of the petals at point of attachment is usually 18C, sometimes 18B. Underside of petals is generally pale or off-white coloring but sometimes darker, approaching 18C. General tonality from a distance is most often soft apricot yellow.

C. Petals:

(1) *Texture.*—Thick.

(2) *Appearance.*—Inside — satiny; outside — satiny.

(3) *Form.*—Oval with petals distinctly reflexing to points and tilting downward.

(4) *Arrangement.*—Regularly arranged, shingle-like.

(5) *Petaloids in center.*—Few.

(6) *Persistence.*—Drop cleanly.

(7) *Fragrance.*—Slight, sweet.

(8) *Lasting quality.*—Moderately long on plant and when cut.

REPRODUCTIVE ORGANS

A. Stamens, filaments and anthers:

(1) *Arrangement.*—Stamens regularly arranged around styles.

(2) *Color.*—15B.

B. Pollen: Color — 15A.

C. Styles: Medium to short, close cluster.

D. Stigmas: Color — 46D.

E. Hips: Shape — none observed.

PLANT

A. Form: Compact, spreading.

B. Growth: Vigorous, well branched.

*Height attained.*—12 to 15 inches.

C. Foliage: Compound 5 to 7 leaflet leaves.

(1) *Size.*—Medium.

(2) *Quantity.*—Abundant.

(3) *Color.*—New foliage: Upper side — 138A. Under side — 191B. Old foliage: Upper side — 133A. Under side — 139C.

(4) *Shape.*—Pointed, oval.

(5) *Texture.*—Upper side — satiny. Under side — matte.

(6) *Edge.*—Serrated.

(7) *Serration.*—Relatively deeper toward tips of leaflets.

(8) *Leaf stem.*—Color — near to 138A. Under side — near to 144A.

(9) *Stipules.*—Medium length, slightly bearded.

(10) *Resistance to disease.*—Blackspot — good. Mildew — good.

D. Wood:

(1) *New wood.*—Color — near 143A. Bark — smooth.

(2) *Old wood.*—Color — near to 137B. Bark — smooth.

E. Thorns:

(1) *Thorns.*—Quantity — ordinary. On laterals from stalk — normal. Form — long thin point. Length — long. Color (when young) — 70B. Position — irregular.

(2) *Prickles.*—None.

F. Winter Hardiness: Needs some protection in extreme climate.

I claim:

1. A new and distinct variety of rose plant of the miniature class, substantially as shown and described, characterized particularly by beautiful unusual salmon and carrot red blooms borne primarily singly to a stem.

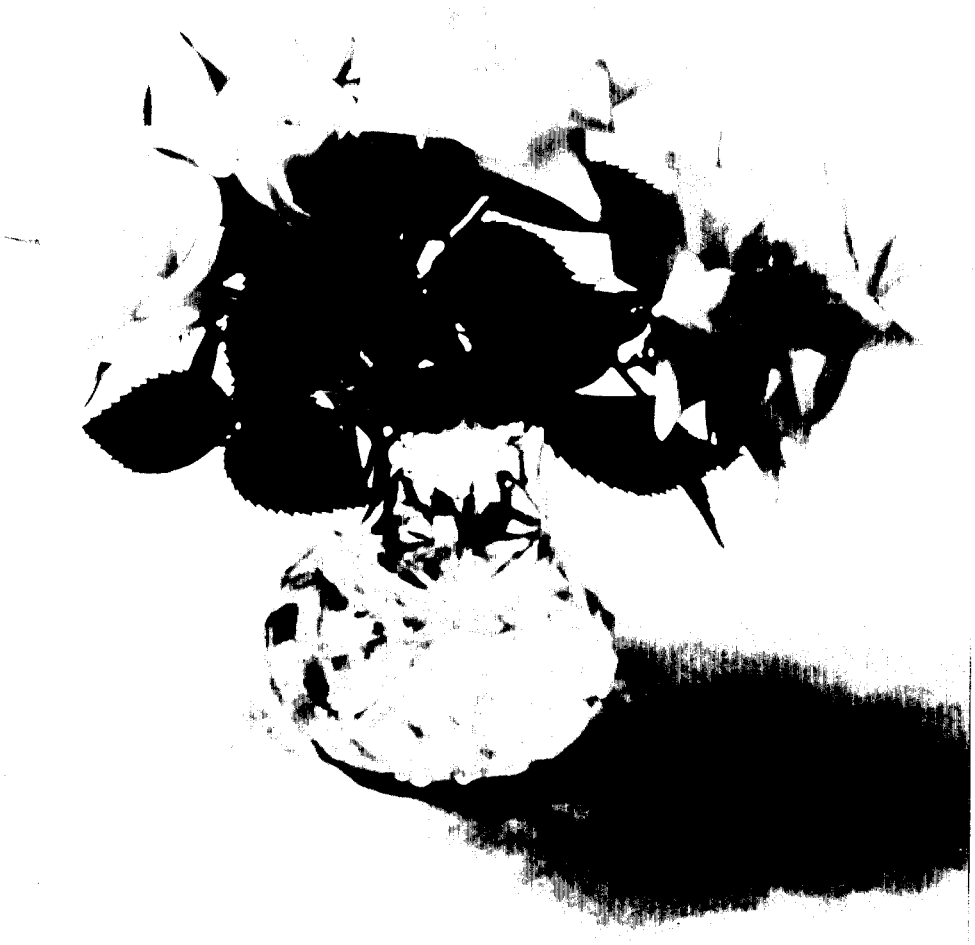

* * * * *